United States Patent
Inagawa et al.

(10) Patent No.: US 12,113,394 B2
(45) Date of Patent: Oct. 8, 2024

(54) AUXILIARY POWER SUPPLY DEVICE, POWER SUPPLY DEVICE, AND MEDICAL SYSTEM

(71) Applicant: TDK CORPORATION, Tokyo (JP)

(72) Inventors: Takumi Inagawa, Tokyo (JP); Yuuta Takano, Tokyo (JP)

(73) Assignee: TDK CORPORATION, Tokyo (JP)

( * ) Notice: Subject to any disclaimer, the term of this patent is extended or adjusted under 35 U.S.C. 154(b) by 263 days.

(21) Appl. No.: 17/751,381

(22) Filed: May 23, 2022

(65) Prior Publication Data

US 2022/0385099 A1 Dec. 1, 2022

(30) Foreign Application Priority Data

May 28, 2021 (JP) .................. 2021-089726

(51) Int. Cl.
*H02J 9/06* (2006.01)
*A61B 90/00* (2016.01)

(52) U.S. Cl.
CPC .............. *H02J 9/061* (2013.01); *A61B 90/08* (2016.02); *H02J 9/068* (2020.01)

(58) Field of Classification Search
CPC .... H02J 9/061; H02J 9/068; H02J 9/06; H02J 2310/23; H02J 2207/50; A61B 18/1206; H02M 1/00

See application file for complete search history.

(56) References Cited

U.S. PATENT DOCUMENTS

2016/0322845 A1* 11/2016 Lueth .................. H02J 7/00
2019/0044336 A1* 2/2019 Wagner ............... A61B 6/56

FOREIGN PATENT DOCUMENTS

JP H10-004674 A * 1/1998

* cited by examiner

*Primary Examiner* — Daniel Cavallari
*Assistant Examiner* — Rasem Mourad
(74) *Attorney, Agent, or Firm* — Oliff PLC

(57) ABSTRACT

An auxiliary power supply device in which an increase in the size of an entire system including both an auxiliary power supply circuit unit and a sub-power supply circuit unit is able to be curbed is provided. There is provided an auxiliary power supply device configured to be connected to a power supply device, the auxiliary power supply device including: an auxiliary power supply circuit unit configured to supply electric power to the power supply device in a case in which supply of electric power to the power supply device is shut off; and a sub-power supply circuit unit having an input side connected to the power supply device and an output side connected to a load and configured to supply an output voltage to other circuit units in accordance with electric power supplied from the power supply device.

11 Claims, 5 Drawing Sheets

AUXILIARY POWER SUPPLY DEVICE, POWER SUPPLY DEVICE, AND MEDICAL SYSTEM

BACKGROUND OF THE INVENTION

Field of the Invention

The present invention relates to an auxiliary power supply device, a power supply device, and a medical system.

Priority is claimed on Japanese Patent Application No. 2021-089726, filed May 28, 2021, the content of which is incorporated herein by reference.

Description of Related Art

Technologies for protecting a load connected to a power supply device in a case in which supply of power to the power supply device is shut off in accordance with the influence of a power failure or the like have been researched and developed.

In relation with this, a power supply device that has a smoothing circuit unit and in which a second electrostatic capacitor is able to be added, as an auxiliary power supply device, to a first electrostatic capacitor of the smoothing circuit unit is known (see Patent Document 1). The smoothing circuit unit smooths an output of a rectification circuit unit between an output side of the rectification circuit unit and an input side of a switching power supply unit, and supply a resultant output to the switching power supply unit. The second electrostatic capacitor cause the switching power supply unit in a state in which supply of an AC power to the rectification circuit unit is shut off, to extend an output holding time. The output holding time is a time in which the switching power supply unit can maintain an output in a state in which supply of an AC power to the rectification circuit unit is shut off.

PATENT DOCUMENTS

[Patent Document 1] Japanese Unexamined Patent Application, First Publication No. H10-004674

SUMMARY OF THE INVENTION

In a power supply device, a sub-power supply device is frequently added to the auxiliary power supply device as disclosed in Patent Document 1. However, addition of two devices in which are the auxiliary power supply device and the sub-power supply device to a power supply device may lead to an increase in the size of the power supply device. An increase in the size of the power supply device may lead to a reduction of versatility and thus is not preferable.

The present invention is in consideration of such situations, and an object thereof is to provide an auxiliary power supply device, a power supply device, and a medical system in which increase in the size of an entire system including an auxiliary power supply circuit unit and a sub-power supply circuit unit is able to curbed.

One aspect of the present invention is an auxiliary power supply device configured to be connected to a power supply device, the auxiliary power supply device including: an auxiliary power supply circuit unit configured to supply electric power to the power supply device in a case in which supply of electric power to the power supply device is shut off; and a sub-power supply circuit unit having an input side connected to the power supply device and an output side connected to a load and configured to supply an output voltage to other circuit units in accordance with electric power supplied from the power supply device.

According to the present invention, an increase in the size of an entire system including both an auxiliary power supply circuit unit and a sub-power supply circuit unit can be curbed.

DETAILED DESCRIPTION OF THE INVENTION

Embodiment

Hereinafter, an embodiment of the present invention will be described with reference to the drawings. Here, in the embodiment, a conductor that transmits an electrical signal according to DC (Direct Current) power or an electrical signal according to AC (Alternating Current) power will be referred to as a transmission path in description. For example, the transmission path may be a conductor printed on a substrate, a conductor such as a conductor formed in a line shape, or any other conductor. In the embodiment, a voltage represents an electric potential difference from an electric potential serving as a predetermined reference, and illustration and description of the electric potential serving as the reference will be omitted. Here, the electric potential serving as the reference may be any electric potential. In the embodiment, as an example, a case in which the electric potential serving as the reference is a ground electric potential will be described. In addition, in the embodiment, for the convenience of description, a state in which a current is flowing between a collector terminal and an emitter terminal among states of a certain phototransistor will be referred to as an on state in description. Furthermore, in the embodiment, for the convenience of description, a state in which a current is not flowing between the collector terminal and the emitter terminal among states of a certain photo transistor will be referred to as an off state in description.

<Configuration of Power Supply System>

Figure 1:
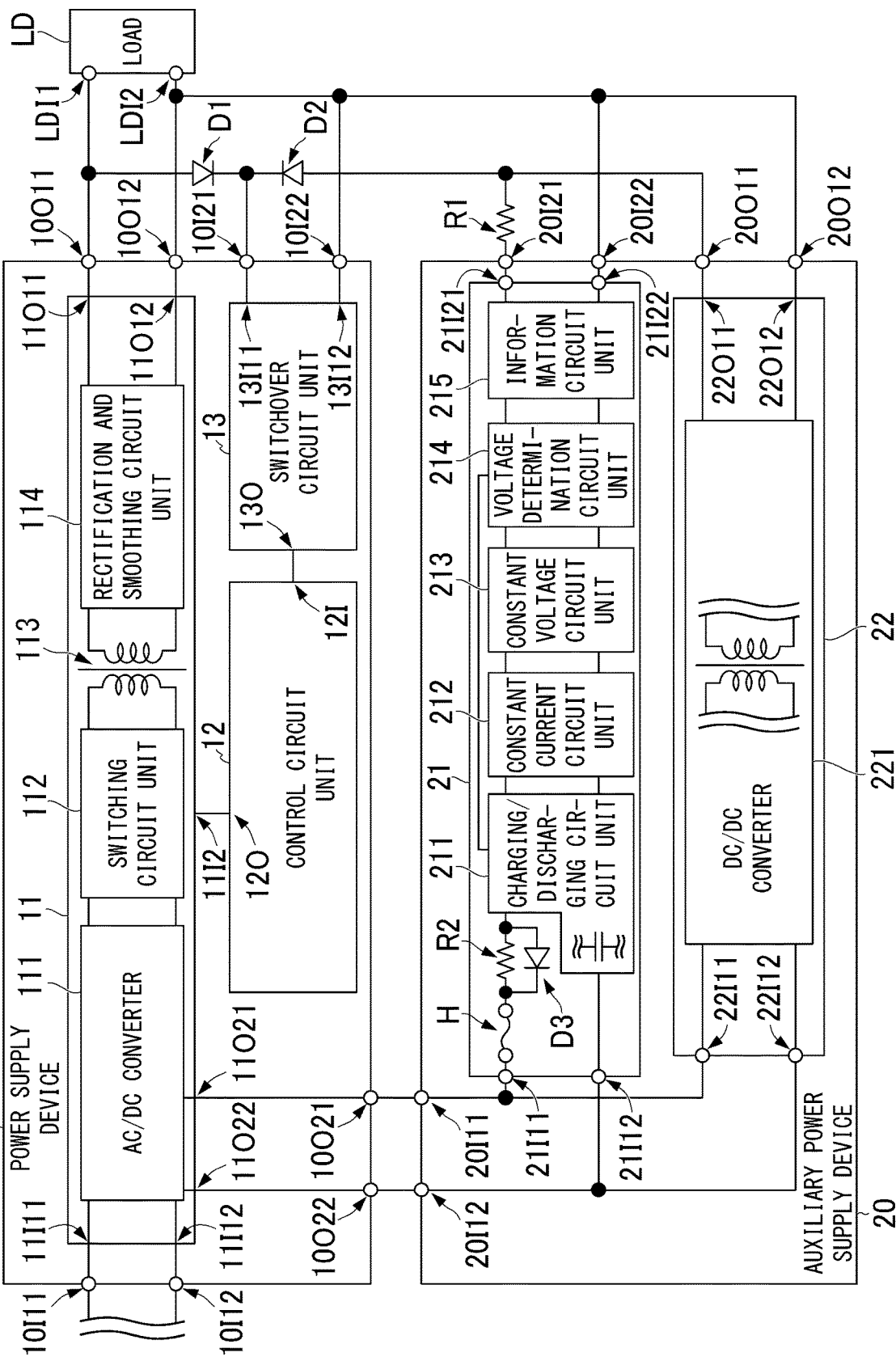
FIG. 1 is a diagram illustrating an example of the configuration of a power supply system 1 according to an embodiment.

Hereinafter, the configuration of a power supply system 1 according to the embodiment will be described with reference to FIG. 1. FIG. 1 is a diagram illustrating an example of the configuration of the power supply system 1 according to the embodiment.

The power supply system 1 supplies a voltage of a magnitude determined in advance to a load LD based on a voltage supplied from an external power supply P. In FIG. 1, for the convenience of description, the power supply P is omitted.

Hereinafter, a case in which the power supply P is a commercial power supply that supplies an AC voltage to a power supply device 10 will be described as an example. In addition, hereinafter, a case in which the power supply system 1 supplies a DC voltage to the load LD will be described as an example. The power supply P may be another power supply that supplies an AC voltage to the power supply device 10 in place of the commercial power supply. In addition, the power supply P may be another power supply that supplies a DC voltage to the power supply device 10 in place of the power supply supplying an AC voltage to the power supply device 10. Furthermore, the power supply system 1 may be configured to supply an AC voltage to the load LD instead of having the configuration of supplying a DC voltage to the load LD.

The load LD may be any device as long as it is a device to which a DC power is supplied from the power supply system 1. For example, the load LD may be a motor, a storage battery, or the like.

The power supply system 1 includes a power supply device 10, an auxiliary power supply device 20, a resistance element R1, a diode D1, and a diode D2. The power supply system 1 may be configured to include another circuit element, another circuit, another device, another member, and the like in addition to these components. In addition, the power supply system 1 may be configured not to include some or all of the resistance element R1, the diode D1, and the diode D2. In the example illustrated in FIG. 1, in the power supply system 1, the power supply device 10, the auxiliary power supply device 20, the resistance element R1, the diode D1, and the diode D2 are configured as separate bodies. However, in the power supply system 1, some or all of the power supply device 10, the auxiliary power supply device 20, the resistance element R1, the diode D1, and the diode D2 may be integrally configured. In addition, the power supply system 1 may be configured to include a load LD in addition to the power supply device 10, the auxiliary power supply device 20, the resistance element R1, the diode D1, and the diode D2. In such a case, the load LD may be integrally configured with some or all of the power supply device 10, the auxiliary power supply device 20, the resistance element R1, the diode D1, and the diode D2.

First, an example of a connection pattern of the power supply device 10, the auxiliary power supply device 20, the load LD, the resistance element R1, the diode D1, and the diode D2 in the power supply system 1 will be described.

The power supply device 10 has eight terminals including a power supply terminal 10I11, a power supply terminal 10I12, an input terminal 10I21, an input terminal 10I22, an output terminal 10O11, an output terminal 10O12, an output terminal 10O21, and an output terminal 10O22. In addition, the power supply device 10 may be configured to have other terminals in addition to these eight terminals.

The auxiliary power supply device 20 has six terminals including a power supply terminal 20I11, a power supply terminal 20I12, an input terminal 20I21, an input terminal 20I22, an output terminal 20O11, and an output terminal 20O12. In addition, the auxiliary power supply device 20 may be configured to include other terminals in addition to these six terminals.

The load LD has two terminals including a power supply terminal LDI1 and a power supply terminal LDI2. In addition, the load LD may be configured to include other terminals in addition to these two terminals.

The power supply terminal 10I11 of the power supply device 10 is a terminal that is connected to one of two output terminals included in the power supply P through a transmission line. In addition, other circuit elements, other circuits, other devices, other members, and the like may be configured to be provided between the power supply terminal 10I11 and the power supply P unless the function of the power supply system 1 is impaired.

The power supply terminal 10I12 of the power supply device 10 is a terminal that is connected to the other of the two output terminals included in the power supply P through a transmission line. In addition, other circuit elements, other circuits, other devices, other members, and the like may be configured to be provided between the power supply terminal 10I12 and the power supply P unless the function of the power supply system 1 is impaired.

The output terminal 10O11 of the power supply device 10 is connected to the power supply terminal LDI1 of the load LD through a transmission line. In addition, other circuit elements, other circuits, other devices, other members, and the like may be configured to be provided between the output terminal 10O11 and the power supply terminal LDI1 unless the function of the power supply system 1 is impaired.

A transmission line connecting the output terminal 10O11 of the power supply device 10 and the power supply terminal LDI1 of the load LD is connected to an anode of the diode D1 through another transmission line. In addition, other circuit elements, other circuits, other devices, other members, and the like may be configured to be provided between the transmission line connecting the output terminal 10O11 and the power supply terminal LDI1 and the diode D1 unless the function of the power supply system 1 is impaired.

A cathode of the diode D1 is connected to the input terminal 10I21 of the power supply device 10 and a cathode of the diode D2 through a transmission line. In addition, other circuit elements, other circuits, other devices, other members, and the like may be configured to be provided between the diode D1 and the input terminal 10I21 unless the function of the power supply system 1 is impaired. Furthermore, other circuit elements, other circuits, other devices, other members, and the like may be configured to be provided between the diode D1 and the diode D2 unless the function of the power supply system 1 is impaired.

An anode of the diode D2 is connected to one of the two terminals included in the resistance element R1 and the output terminal 20O11 of the auxiliary power supply device 20 through a transmission line. In addition, other circuit elements, other circuits, other devices, other members, and the like may be configured to be provided between the diode D2 and the resistance element R1 unless the function of the power supply system 1 is impaired. Furthermore, other circuit elements, other circuits, other devices, other members, and the like may be configured to be provided between the diode D2 and the output terminal 20O11 unless the function of the power supply system 1 is impaired.

The other of the two terminals included in the resistance element R1 is connected to the input terminal 20I21 of the auxiliary power supply device 20 through a transmission line. In addition, other circuit elements, other circuits, other devices, other members, and the like may be configured to be provided between the resistance element R1 and the input terminal 20I21 unless the function of the power supply system 1 is impaired.

The output terminal 10O12 of the power supply device 10 is connected to the power supply terminal LDI2 of the load LD through a transmission line. In addition, other circuit elements, other circuits, other devices, other members, and the like may be configured to be provided between the output terminal 10O12 and the power supply terminal LDI2 unless the function of the power supply system 1 is impaired.

The transmission line connecting the output terminal 11O12 of the power supply device 10 and the power supply terminal LDI2 of the load LD are respectively connected to the input terminal 10I22 of the power supply device 10, the input terminal 20I22 of the auxiliary power supply device 20, and the output terminal 20O12 of the auxiliary power supply device 20 through different transmission lines. In addition, other circuit elements, other circuits, other devices, other members, and the like may be configured to be provided between the transmission line connecting the output terminal 11O12 and the power supply terminal LDI2 and the input terminal 10I22 unless the function of the power supply system 1 is impaired. Furthermore, other circuit elements, other circuits, other devices, other members, and the like may be configured to be provided between the transmission line connecting the output terminal 11O12 and the power supply terminal LDI2 and the input terminal 20I22 unless the function of the power supply system 1 is impaired. In addition, other circuit elements, other circuits, other devices, other members, and the like may be configured to be provided between the transmission line connecting the output terminal 11O12 and the power supply terminal LDI2 and the output terminal 20O12 unless the function of the power supply system 1 is impaired.

The output terminal 10O21 of the power supply device 10 is connected to the power supply terminal 20I11 of the auxiliary power supply device 20 through a transmission line. In addition, other circuit elements, other circuits, other devices, other members, and the like may be configured to be provided between the output terminal 10O21 and the power supply terminal 20I11 unless the function of the power supply system 1 is impaired.

The output terminal 10O22 of the power supply device 10 is connected to the power supply terminal 20I12 of the auxiliary power supply device 20 through a transmission line. In addition, other circuit elements, other circuits, other devices, other members, and the like may be configured to be provided between the output terminal 10O22 and the power supply terminal 20I12 unless the function of the power supply system 1 is impaired.

Next, the configuration of the power supply device 10 will be described.

The power supply device 10 includes a power supply circuit unit 11, a control circuit unit 12, and a switchover circuit unit 13. In addition, the power supply device 10 may be configured to include other circuit elements, other circuits, other devices, other members, and the like in addition to these three circuit units.

The power supply circuit unit 11 includes seven terminals including a power supply terminal 11I11, a power supply terminal 11I12, an input terminal 11I2, an output terminal 11O11, an output terminal 11O12, an output terminal 11O21, and an output terminal 11O22. In addition, the power supply circuit unit 11 may be configured to have other terminals in addition to these seven terminals.

The control circuit unit 12 has two terminals including an input terminal 12I and an output terminal 12O. In addition, the control circuit unit 12 may be configured to have other terminals in addition to these two terminals.

The switchover circuit unit 13 has three terminals including an input terminal 13I11, an input terminal 13I12, and an output terminal 13O. In addition, the switchover circuit unit 13 may be configured to have other terminals in addition to these three terminals.

The power supply terminal 11I11 of the power supply circuit unit 11 is connected to the power supply terminal 10I11 of the power supply device 10 through a transmission line. In addition, other circuit elements, other circuits, other devices, other members, and the like may be configured to be provided between the power supply terminal 11I11 and the power supply terminal 10I11 unless the function of the power supply system 1 is impaired.

The power supply terminal 11I12 of the power supply circuit unit 11 is connected to the power supply terminal 10I12 of the power supply device 10 through a transmission line. In addition, other circuit elements, other circuits, other devices, other members, and the like may be configured to be provided between the power supply terminal 11I12 and the power supply terminal 10I12 unless the function of the power supply system 1 is impaired.

The output terminal 11O11 of the power supply circuit unit 11 is connected to the output terminal 10O11 of the power supply device 10 through a transmission line. In addition, other circuit elements, other circuits, other devices, other members, and the like may be configured to be provided between the output terminal 11O11 and the output terminal 10O11 unless the function of the power supply system 1 is impaired.

The output terminal 11O12 of the power supply circuit unit 11 is connected to the output terminal 10O12 of the power supply device 10 through a transmission line. In addition, other circuit elements, other circuits, other devices, other members, and the like may be configured to be provided between the output terminal 11O12 and the output terminal 10O12 unless the function of the power supply system 1 is impaired.

The output terminal 11O21 of the power supply circuit unit 11 is connected to the output terminal 10O21 of the power supply device 10 through a transmission line. In addition, other circuit elements, other circuits, other devices, other members, and the like may be configured to be provided between the output terminal 11O21 and the output terminal 10O21 unless the function of the power supply system 1 is impaired.

The output terminal 11O22 of the power supply circuit unit 11 is connected to the output terminal 10O22 of the power supply device 10 through a transmission line. In addition, other circuit elements, other circuits, other devices, other members, and the like may be configured to be provided between the output terminal 11O22 and the output terminal 10O22 unless the function of the power supply system 1 is impaired.

The input terminal 11I2 of the power supply circuit unit 11 is connected to the output terminal 12O of the control circuit unit 12 through a transmission line. In addition, other circuit elements, other circuits, other devices, other members, and the like may be configured to be provided between the input terminal 11I2 and the output terminal 12O unless the function of the power supply system 1 is impaired.

The input terminal 12I of the control circuit unit 12 is connected to the output terminal 13O of the switchover circuit unit 13 through a transmission line. In addition, other circuit elements, other circuits, other devices, other members, and the like may be configured to be provided between the input terminal 12I and the output terminal 13O unless the function of the power supply system 1 is impaired.

The input terminal 13I11 of the switchover circuit unit 13 is connected to the input terminal 10I21 of the power supply device 10 through a transmission line. In addition, other circuit elements, other circuits, other devices, other members, and the like may be configured to be provided between the input terminal 13I11 and the input terminal 10I21 unless the function of the power supply system 1 is impaired.

The input terminal 13I12 of the switchover circuit unit 13 is connected to the input terminal 10I22 of the power supply device 10 through a transmission line. In addition, other circuit elements, other circuits, other devices, other members, and the like may be configured to be provided between the input terminal 13I12 and the input terminal 10I22 unless the function of the power supply system 1 is impaired.

Next, the configuration of the power supply circuit unit 11 will be described.

The power supply circuit unit 11 may have any configuration as long as the configuration is able to convert an AC voltage supplied from the power supply P into a DC voltage and output the DC voltage after conversion. Hereinafter, as illustrated in FIG. 1, a case in which the power supply circuit unit 11 includes an AC (Alternating Current)/DC (Direct Current) converter 111, a switching circuit unit 112, a transformer 113, and a rectification and smoothing circuit unit 114 will be described as an example. In a case in which a DC voltage is supplied from the power supply P, the power supply circuit unit 11 includes a DC/DC converter in place of the AC/DC converter 111. In other words, the power supply circuit unit 11 includes a converter that converts a voltage supplied from the power supply P into a DC voltage. The AC/DC converter 111 is one example of this converter.

One of two power supply terminals included in the AC/DC converter 111 is connected to the power supply terminal 11I11 of the power supply circuit unit 11 through a transmission line. In addition, other circuit elements, other circuits, other devices, other members, and the like may be configured to be provided between the AC/DC converter 111 and the power supply terminal 11I11 unless the function of the power supply system 1 is impaired.

The other of the two power supply terminals included in the AC/DC converter 111 is connected to the power supply terminal 11I12 of the power supply circuit unit 11 through a transmission line. In addition, other circuit elements, other circuits, other devices, other members, and the like may be configured to be provided between the AC/DC converter 111 and the power supply terminal 11I12 unless the function of the power supply system 1 is impaired.

In addition, an output terminal on a high electric potential side among two output terminals included in the AC/DC converter 111 is connected to a power supply terminal on a high electric potential side among two power supply terminals included in the switching circuit unit 112 and the output terminal 11O21 of the power supply circuit unit 11 through a transmission line. In addition, other circuit elements, other circuits, other devices, other members, and the like may be configured to be provided between this output terminal and this power supply terminal unless the function of the power supply system 1 is impaired. Furthermore, other circuit elements, other circuits, other devices, other members, and the like may be configured to be provided between the AC/DC converter 111 and the output terminal 11O21 unless the function of the power supply system 1 is impaired.

In addition, an output terminal on a low electric potential side among the two output terminals included in the AC/DC converter 111 is connected to a power supply terminal on a low electric potential side among the two power supply terminals included in the switching circuit unit 112 and the output terminal 11O22 of the power supply circuit unit 11 through a transmission line. Furthermore, other circuit elements, other circuits, other devices, other members, and the like may be configured to be provided between this output terminal and this power supply terminal unless the function of the power supply system 1 is impaired. In addition, other circuit elements, other circuits, other devices, other members, and the like may be configured to be provided between the AC/DC converter 111 and the output terminal 11O22 unless the function of the power supply system 1 is impaired.

In other words, an input side of the AC/DC converter 111 is connected to the power supply P through these power supply terminals. As a result, an AC voltage is supplied from the power supply P to the AC/DC converter 111. The AC/DC converter 111 converts the AC voltage supplied from the power supply P into a DC voltage. The AC/DC converter 111 supplies the DC voltage after conversion to the switching circuit unit 112 and applies the DC voltage between the output terminal 10O21 and the output terminal 10O22. In other words, the AC/DC converter 111 supplies the DC voltage after conversion to the switching circuit unit 112 and the auxiliary power supply device 20.

The AC/DC converter 111, for example, may be composed of a combination of a PFC (power factor correction) circuit (a power factor improvement circuit) and a DC/DC converter, may be composed of a combination of a rectification circuit and a DC/DC converter, or may be composed of another circuit. Hereinafter, as an example, a case in which the AC/DC converter 111 includes a smoothing capacitor together with a rectification circuit will be described. Hereinafter, for the convenience of description, this smoothing capacitor will be referred to as a first smoothing capacitor.

One of two output terminals included in the switching circuit unit 112 is connected to one of two terminals included in a primary winding of the transformer 113 through a transmission line. In addition, the other of the two output terminals included in the switching circuit unit 112 is connected to the other of the two terminals included in the primary winding of the transformer 113 through a transmission line. Furthermore, other circuit elements, other circuits, other devices, other members, and the like may be configured to be provided between the switching circuit unit 112 and the primary winding of the transformer 113 unless the function of the power supply system 1 is impaired.

The switching circuit unit 112 converts a DC voltage generated by the AC/DC converter 111 into an AC voltage according to control by the control circuit unit 12. The switching circuit unit 112 supplies the AC voltage after conversion to the primary winding of the transformer 113.

For example, the switching circuit unit 112 is a switching circuit (for example, a full bridge circuit, a half bridge circuit, or the like) in which switching elements (for example, field effect transistors, bipolar transistors, and the like) are connected in a bridge pattern.

One of terminals included in a secondary winding of the transformer 113 is connected to a power supply terminal on a high electric potential side among two power supply terminals included in the rectification and smoothing circuit unit 114 through a transmission line. In addition, other circuit elements, other circuits, other devices, other members, and the like may be configured to be provided between the secondary winding of the transformer 113 and this power supply terminal unless the function of the power supply system 1 is impaired.

The other of the terminals included in the secondary winding of the transformer 113 is connected to a power supply terminal on a low electric potential side among the two power supply terminals included in the rectification and smoothing circuit unit 114 through a transmission line. In addition, other circuit elements, other circuits, other devices, other members, and the like may be configured to be provided between the secondary winding of the transformer 113 and this power supply terminal unless the function of the power supply system 1 is impaired.

The transformer 113 transmits an AC voltage supplied from the switching circuit unit 112, from the primary winding of the transformer 113 to the secondary winding of the transformer 113, based on the law of electromagnetic induction. The secondary winding of the transformer 113 supplies the transmitted AC voltage to the rectification and smoothing circuit unit 114.

An output terminal on a high electric potential side among two output terminals included in the rectification and smoothing circuit unit 114 is connected to the output terminal 11O11 of the power supply circuit unit 11 through a transmission line. In addition, other circuit elements, other circuits, other devices, other members, and the like may be configured to be provided between this output terminal and the output terminal 11O11 unless the function of the power supply system 1 is impaired.

An output terminal on a low electric potential side among the two output terminals included in the rectification and smoothing circuit unit 114 is connected to the output terminal 11O12 of the power supply circuit unit 11 through a transmission line. In addition, other circuit elements, other circuits, other devices, other members, and the like may be configured to be provided between this output terminal and the output terminal 11O12 unless the function of the power supply system 1 is impaired.

The rectification and smoothing circuit unit 114 converts an AC voltage supplied from the secondary winding of the transformer 113 into a DC voltage. The rectification and smoothing circuit unit 114 applies the converted DC voltage between the output terminal 10O11 and the output terminal 10O12 of the power supply device 10 through the output terminal 11O11 and the output terminal 11O12. In other words, the rectification and smoothing circuit unit 114 supplies the converted DC voltage to the load LD and the switchover circuit 13.

For example, the rectification and smoothing circuit unit 114 is composed of a rectification diode not illustrated and a smoothing capacitor not illustrated.

Next, the configuration of the control circuit unit 12 will be described.

The control circuit unit 12 controls the power supply circuit unit 11. More specifically, the control circuit unit 12 controls the switching circuit unit 112 included in the power supply circuit unit 11 and performs switching of switching elements included in the switching circuit unit 112.

In a case in which an enable signal is output from the switchover circuit unit 13, the control circuit unit 12 is enabled. In a case in which the control circuit unit 12 is enabled, the control circuit unit 12 performs control of the power supply circuit unit 11. On the other hand, in a case in which an enable signal has not been output from the switchover circuit unit 13, the control circuit unit 12 is disabled. In a case in which the control circuit unit 12 is disabled, the control circuit unit 12 does not perform control of the power supply circuit unit 11.

Next, the configuration of the switchover circuit unit 13 will be described.

In a case in which a DC voltage of a magnitude determined in advance or more is supplied from at least one of the power supply circuit unit 11 and the auxiliary power supply device 20 through the input terminal 13I11 and the input terminal 13I12, the switchover circuit unit 13 outputs an enable signal to the control circuit unit 12. In other words, in accordance with whether or not an enable signal is output, the switchover circuit unit 13 causes the control circuit unit 12 to perform switching between enabling and disabling of the control circuit unit 12. The switchover circuit unit 13 may be referred to as a remote control unit. In addition, the magnitude determined in advance is, for example, a magnitude of a voltage output from the auxiliary power supply device 20 but is not limited thereto.

Next, the configuration of the auxiliary power supply device 20 will be described.

The auxiliary power supply device 20 includes an auxiliary power supply circuit unit 21 and a sub-power supply circuit unit 22. In addition, the auxiliary power supply device 20 may be configured to include other circuit elements, other circuits, other devices, other members, and the like in addition to these two circuit units.

The auxiliary power supply circuit unit 21 has four terminals including a power supply terminal 21I11, a power supply terminal 21I12, an input terminal 21I21, and an input terminal 21I22. In addition, the auxiliary power supply circuit unit 21 may be configured to have other terminals in addition to these four terminals.

The sub-power supply circuit unit 22 has four terminals including a power supply terminal 22I11, a power supply terminal 22I12, an output terminal 22O11, and an output terminal 22O12. In addition, the sub-power supply circuit unit 22 may be configured to have other terminals in addition to these four terminals.

The power supply terminal 21I11 of the auxiliary power supply circuit unit 21 is connected to the power supply terminal 20I11 of the auxiliary power supply device 20 and the power supply terminal 22I11 of the sub-power supply circuit unit 22 through a transmission line. In addition, other circuit elements, other circuits, other devices, other members, and the like may be configured to be provided between the power supply terminal 21I11 and the power supply terminal 20I11 unless the function of the power supply system 1 is impaired. Furthermore, other circuit elements, other circuits, other devices, other members, and the like may be configured to be provided between the power supply terminal 21I11 and the power supply terminal 22I11 unless the function of the power supply system 1 is impaired.

The power supply terminal 21I12 of the auxiliary power supply circuit unit 21 is connected to the power supply terminal 20I12 of the auxiliary power supply device 20 and the power supply terminal 22I12 of the sub-power supply circuit unit 22 through a transmission line. In addition, other circuit elements, other circuits, other devices, other members, and the like may be configured to be provided between the power supply terminal 21I12 and the power supply terminal 20I12 unless the function of the power supply system 1 is impaired. Furthermore, other circuit elements, other circuits, other devices, other members, and the like may be configured to be provided between the power supply terminal 21I12 and the power supply terminal 22I12 unless the function of the power supply system 1 is impaired.

The input terminal 21I21 of the auxiliary power supply circuit unit 21 is connected to the input terminal 20I21 of the auxiliary power supply device 20 through a transmission line. In addition, other circuit elements, other circuits, other devices, other members, and the like may be configured to be provided between the input terminal 21I21 and the input terminal 20I21 unless the function of the power supply system 1 is impaired.

The input terminal 21I22 of the auxiliary power supply circuit unit 21 is connected to the input terminal 20I22 of the auxiliary power supply device 20 through a transmission line. In addition, other circuit elements, other circuits, other devices, other members, and the like may be configured to be provided between the input terminal 21I22 and the input terminal 20I22 unless the function of the power supply system 1 is impaired.

The output terminal 22O11 of the sub-power supply circuit unit 22 is connected to the output terminal 20O11 of the auxiliary power supply device 20 through a transmission line. In addition, other circuit elements, other circuits, other devices, other members, and the like may be configured to be provided between the output terminal 22O11 and the output terminal 20O11 unless the function of the power supply system 1 is impaired.

The output terminal 22O12 of the sub-power supply circuit unit 22 is connected to the output terminal 20O12 of the auxiliary power supply device 20 through a transmission line. In addition, other circuit elements, other circuits, other devices, other members, and the like may be configured to be provided between the output terminal 22O12 and the output terminal 20O12 unless the function of the power supply system 1 is impaired.

Next, the configuration of the auxiliary power supply circuit unit 21 will be described.

In a case in which supply of electric power to the power supply device 10 is shut off, the auxiliary power supply circuit unit 21 supplies electric power to the power supply device 10. The auxiliary power supply circuit unit 21 may have any configuration as long as it is a configuration in which electric power can be supplied to the power supply device 10 in a case in which supply of electric power to the power supply device 10 is shut off. Hereinafter, as one example, as illustrated in FIG. 1, a case in which the auxiliary power supply circuit unit 21 includes a fuse H, a resistance element R2, a diode D3, a charging/discharging circuit unit 211, a constant current circuit unit 212, a constant voltage circuit unit 213, a voltage determination circuit unit 214, and a information circuit unit 215 will be described.

One of two terminals included in the fuse H is connected to the power supply terminal 21I11 of the auxiliary power supply circuit unit 21 through a transmission line. In addition, other circuit elements, other circuits, other devices, other members, and the like may be configured to be provided between the fuse H and the power supply terminal 21I11 unless the function of the power supply system 1 is impaired.

The other of the two terminals included in the fuse H is connected to one of two terminals included in the resistance element R2 and a cathode of the diode D3 through a transmission line. In addition, other circuit elements, other circuits, other devices, other members, and the like may be configured to be provided between the fuse H and the resistance element R2 unless the function of the power supply system 1 is impaired. Furthermore, other circuit elements, other circuits, other devices, other members, and the like may be configured to be provided between the fuse H and the diode D3 unless the function of the power supply system 1 is impaired. In addition, other circuit elements, other circuits, other devices, other members, and the like may be configured to be provided between the resistance element R2 and the cathode of the diode D3 unless the function of the power supply system 1 is impaired.

The other of the two terminals included in the resistance element R2 is connected to an anode of the diode D3 and a power supply terminal on a high electric potential side among two power supply terminals included in the charging/discharging circuit unit 211 through a transmission line. In addition, other circuit elements, other circuits, other devices, other members, and the like may be configured to be provided between the resistance element R2 and the anode of the diode D3 unless the function of the power supply system 1 is impaired. Furthermore, other circuit elements, other circuits, other devices, other members, and the like may be configured to be provided between the resistance element R2 and the charging/discharging circuit unit 211 unless the function of the power supply system 1 is impaired. In addition, other circuit elements, other circuits, other devices, other members, and the like may be configured to be provided between the diode D3 and the charging/discharging circuit unit 211 unless the function of the power supply system 1 is impaired.

In this way, the resistance element R2 is connected in parallel with the diode D3 between the power supply terminal 20I11 of the auxiliary power supply device 20 and the charging/discharging circuit unit 211. A direction in which a current is caused to flow by the diode D3 is a direction from the charging/discharging circuit unit 211 to the power supply terminal 20I11.

In addition, the resistance element R2 may be configured to be connected in parallel with the diode D3 between the power supply terminal 20I12 of the auxiliary power supply device 20 and the charging/discharging circuit unit 211. In this case, one of two terminals included in the fuse H is connected to the power supply terminal 21I11 of the auxiliary power supply circuit unit 21 through a transmission line. In addition, the other of the two terminals included in the fuse H is connected to a power supply terminal on a high electric potential side among two power supply terminals included in the charging/discharging circuit unit 211 through a transmission line. Furthermore, one of two terminals included in the resistance element R2 is connected to the power supply terminal 21I12 of the auxiliary power supply circuit unit 21 and the anode of the diode D3 through a transmission line. In addition, the other of the two terminals included in the resistance element R2 is connected to the cathode of the diode D3 and a power supply terminal on a low electric potential side among two power supply terminals included in the charging/discharging circuit unit 211 through a transmission line. A direction in which a current is caused to flow by the diode D3 is a direction from the charging/discharging circuit unit 211 to the power supply terminal 20I11. Here, other circuit elements, other circuits, other devices, other members, and the like may be configured to be provided between the fuse H and the power supply terminal 21I11 unless the function of the power supply system 1 is impaired. In addition, other circuit elements, other circuits, other devices, other members, and the like may be configured to be provided between the fuse H and a power supply terminal on a high electric potential side among the two power supply terminals included in the charging/discharging circuit unit 211 unless the function of the power supply system 1 is impaired. Furthermore, other circuit elements, other circuits, other devices, other members, and the like may be configured to be provided between the power supply terminal 21I12 and the resistance element R2 unless the function of the power supply system 1 is impaired. In addition, other circuit elements, other circuits, other devices, other members, and the like may be configured to be provided between the resistance element R2 and the cathode of the diode D3 unless the function of the power supply system 1 is impaired. Furthermore, other circuit elements, other circuits, other devices, other members, and the like may be configured to be provided between the power supply terminal 21I12 and the anode of the diode D3 unless the function of the power supply system 1 is impaired. In addition, other circuit elements, other circuits, other devices, other members, and the like may be configured to be provided between the resistance element R2 and the cathode of the diode D3 unless the function of the power supply system 1 is impaired. Furthermore, other circuit elements, other circuits, other devices, other members, and the like may be configured to be provided between the resistance element R2 and a power supply terminal on a low electric potential side among the two power supply terminals included in the charging/discharging circuit unit 211 unless the function of the power supply system 1 is impaired. In addition, other circuit elements, other circuits, other devices, other members, and the like may be configured to be provided between the cathode of the diode D3 and a power supply terminal on a low electric potential side among the two power supply terminals included in the charging/discharging circuit unit 211 unless the function of the power supply system 1 is impaired.

The power supply terminal on the low electric potential side among the two power supply terminals included in the charging/discharging circuit unit 211 is connected to the power supply terminal 21I12 of the auxiliary power supply circuit unit 21 through a transmission line. In addition, other circuit elements, other circuits, other devices, other members, and the like may be configured to be provided between the charging/discharging circuit unit 211 and the power supply terminal 21I12 unless the function of the power supply system 1 is impaired.

An output terminal on a high electric potential side among the two output terminals included in the charging/discharging circuit unit 211 is connected to a power supply terminal on a high electric potential side among two power supply terminals included in the constant current circuit unit 212 through a transmission line. In addition, other circuit elements, other circuits, other devices, other members, and the like may be configured to be provided between this output terminal and this power supply terminal unless the function of the power supply system 1 is impaired.

An output terminal on a low electric potential side among two output terminals included in the charging/discharging circuit unit 211 is connected to a power supply terminal on a low electric potential side among two power supply terminals included in the constant current circuit unit 212 through a transmission line. In addition, other circuit elements, other circuits, other devices, other members, and the like may be configured to be provided between this output terminal and this power supply terminal unless the function of the power supply system 1 is impaired.

As illustrated in FIG. 1, the charging/discharging circuit unit 211 includes a capacitor that is charged in accordance with supply of an AC power from the power supply P to the power supply device 10 and discharges a discharge current in accordance with discharge of the first smoothing capacitor of the AC/DC converter 111. Hereinafter, for the convenience of description, this capacitor will be referred to as a first capacitor in description. One of two terminals included in the first capacitor is connected to the power supply terminal on the high electric potential side among the two power supply terminals included in the charging/discharging circuit unit 211 and the output terminal on the high electric potential side among the two output terminals included in the charging/discharging circuit unit 211 through a transmission line. In addition, the other of the two terminals included in the first capacitor is connected to the power supply terminal on the low electric potential side among the two power supply terminals included in the charging/discharging circuit unit 211 and the output terminal on the low electric potential side among the two output terminals included in the charging/discharging circuit unit 211 through a transmission line. For this reason, a direction in which a current is caused to flow by the diode D3 described above can be rephrased as a direction from the high electric potential side of the first capacitor to the power supply terminal 20I11. In addition, in a case in which each of the resistance element R2 and the diode D3 is connected in parallel between the power supply terminal 21I12 of the auxiliary power supply circuit unit 21 and the power supply terminal on the low electric potential side among the two power supply terminals included in the charging/discharging circuit unit 211, it can be rephrased that a direction in which a current caused to flow by the diode D3 is a direction from the high electric potential side of the first capacitor to the power supply terminal 20I11. Here, other circuit elements, other circuits, other devices, other members, and the like may be configured to be provided between the first capacitor and each of the four terminals included in the charging/discharging circuit unit 211 unless the function of the power supply system 1 is impaired.

Here, in a case in which a power failure or the like has occurred, the supply of electric power from the power supply P to the power supply device 10 is shut off, and thus the first smoothing capacitor starts discharging. In other words, in this case, the first capacitor of the charging/discharging circuit unit 211 discharges a discharge current. In other words, as illustrated in FIG. 1, in a case in which one of two terminals included in the first smoothing capacitor and the power supply terminal 20I11 are connected to each other, and the other of the two terminals included in the first smoothing capacitor and the power supply terminal 20I12 are connected to each other, the first capacitor discharges a discharge current in accordance with discharge of the first smoothing capacitor. In this case, this discharge current flows through each of the power supply device 10 for which supply of electric power from the power supply P has been shut off and the constant current circuit unit 212. In accordance with this, the power supply device 10 for which supply of electric power from the power supply P has been shut off in this case can continue supply of the DC voltage to the load LD by being driven based on the discharge current discharged from the first capacitor until a charged voltage of the first capacitor becomes lower than a predetermined voltage. In other words, in a case in which supply of electric power from the power supply P to the power supply device 10 has been shut off, the auxiliary power supply circuit unit 21 can continue supply of a DC voltage to the load LD by the power supply device 10 until the charged voltage of the first capacitor becomes lower than a predetermined voltage in accordance with discharge of a discharge current according to the first capacitor. In addition, in this case, the charged voltage of the first capacitor is supplied to the constant current circuit unit 212.

On the other hand, in a case in which electric power is supplied from the power supply P to the power supply device 10, the first capacitor of the charging/discharging circuit unit 211 is charged. In other words, in a case in which supply of electric power from the power supply P to the power supply device 10 has not been shut off, the first capacitor is charged in accordance with a DC voltage supplied from the AC/DC converter 111. In addition, in this case, the DC voltage supplied from the AC/DC converter 111 is supplied also to the constant current circuit unit 212.

The constant current circuit unit 212 outputs a current of a magnitude determined in advance to the constant voltage circuit unit 213 based on a DC voltage supplied from the first smoothing capacitor or the first capacitor of the charging/discharging circuit unit 211. The constant current circuit unit 212 may have any configuration as long as it is configuration that is able to output a current of a magnitude determined in advance to the constant voltage circuit unit 213 based on this DC voltage. In addition, a connection pattern between the constant current circuit unit 212 and the constant voltage circuit unit 213 may be any connection pattern. In addition, other circuit elements, other circuits, other devices, other members, and the like may be configured to be provided between the constant current circuit unit 212 and the constant voltage circuit unit 213 unless the function of the power supply system 1 is impaired.

The constant voltage circuit unit 213 outputs a voltage of a magnitude determined in advance to the voltage determination circuit unit 214 based on a current output from the constant current circuit unit 212. The constant voltage circuit unit 213 may have a configuration as long as it is a configuration that is able to output this voltage to the voltage determination circuit unit 214 as a reference voltage based on this current. In addition, a connection pattern between the constant voltage circuit unit 213 and the voltage determination circuit unit 214 may be any connection pattern. Furthermore, other circuit elements, other circuits, other devices, other members, and the like may be configured to be provided between the constant voltage circuit unit 213 and the voltage determination circuit unit 214 unless the function of the power supply system 1 is impaired.

The voltage determination circuit unit 214 compares a reference voltage generated based on a voltage output from the constant voltage circuit unit 213 and a detected voltage generated based on a charged voltage of the first capacitor of the charging/discharging circuit unit 211 with each other. More specifically, the voltage determination circuit unit 214 determines whether or not this detected voltage is lower than the reference voltage. For this reason, the voltage determination circuit unit 214 is connected to the high electric potential-side output terminal of the charging/discharging circuit unit 211 through a transmission line. In accordance with this, the voltage determination circuit unit 214 can detect the detected voltage generated based on the charged voltage of the first capacitor. A method for generating this detected voltage based on the charged voltage of the first capacitor may be any method. For example, the charged voltage of the first capacitor is converted into a detected voltage by being divided using a resistance element connected on a transmission line connecting the high electric potential-side output terminal of the charging/discharging circuit unit 211 and the voltage determination circuit unit 214. In addition, a method for generating a reference voltage based on a voltage output from the constant voltage circuit unit 213 may be any method. For example, the voltage output from the constant voltage circuit unit 213 is converted into a reference voltage by being divided using a resistance element connected on a transmission line connecting the constant voltage circuit unit 213 and the voltage determination circuit unit 214. Here, for example, this reference voltage is a lowest voltage among voltages that are able to drive the power supply device 10 in a case in which supply of electric power from the power supply P is shut off. In addition, this reference voltage may be a voltage higher than the lowest voltage among voltages that are able to drive the power supply device 10 in a case in which supply of electric power from the power supply P is shut off.

In addition, the voltage determination circuit unit 214 may be configured to compare the reference voltage generated based on the voltage output from the constant voltage circuit unit 213 and the detected voltage generated based on the charged voltage of the first smoothing capacitor of the power supply circuit unit 11 with each other. More specifically, the voltage determination circuit unit 214 may be configured to determine whether or not this detected voltage is lower than the reference voltage. In such a case, the voltage determination circuit unit 214 is connected to a transmission line electrically connecting a cathode of a diode of which an anode is connected to the high electric potential side power supply terminal of the charging/discharging circuit unit 211 and the power supply terminal 21I11 through a transmission line. In accordance with this, the voltage determination circuit unit 214 can detect a detected voltage generated based on the charged voltage of the first smoothing capacitor. In addition, the method for generating this detected voltage based on the charged voltage of the first smoothing capacitor may be any method. For example, the charged voltage of the first smoothing capacitor is converted into the detected voltage by being divided using a resistance element connected on a transmission line connecting this transmission line and the voltage determination circuit unit 214.

In a case in which it is determined that the charged voltage of the first capacitor of the charging/discharging circuit unit 211 is equal to or higher than the reference voltage output from the constant voltage circuit unit 213, the voltage determination circuit unit 214 outputs a signal of which a signal level is a level L to the information circuit unit 215. On the other hand, in a case in which it is determined that the charged voltage of the first capacitor is lower than the reference voltage output from the constant voltage circuit unit 213, the voltage determination circuit unit 214 outputs a signal of which a signal level is a level H to the information circuit unit 215. In other words, the voltage determination circuit unit 214 outputting a signal of the level L represents that an output of a DC voltage from the power supply device 10 stops. In addition, the voltage determination circuit unit 214 outputting a signal of the level H represents that an output of a DC voltage from the power supply device 10 has not stopped. A connection pattern between the voltage determination circuit unit 214 and the information circuit unit 215 may be any connection pattern. In addition, other circuit elements, other circuits, other devices, other members, and the like may be configured to be provided between the voltage determination circuit unit 214 and the information circuit unit 215 unless the function of the power supply system 1 is impaired.

The information circuit unit 215 informs of information that indicates a determination result acquired by the voltage determination circuit unit 214. Hereinafter, a case in which the information circuit unit 215 includes a light emitting diode and a photo transistor of which a state is switched between an on state and an off state in accordance with light emission of the light emission diode will be described as an example. In this case, the light emitting diode emits light when a signal of the level L is output from the voltage determination circuit unit 214, and puts out light when a signal of the level H is output from the voltage determination circuit unit 214. In other words, light emission of the light emitting diode indicates that supply of electric power from the power supply P to the power supply device 10 has not stopped. On the other hand, putting-out of light of the light emitting diode indicates that the supply of electric power from the power supply P to the power supply device 10 has stopped. Here, a base terminal of the photo transistor receives light emitted from the light emitting diode. A collector terminal of the photo transistor is connected to the input terminal 21I21 of the auxiliary power supply device 20 through a transmission line. An emitter terminal of the photo transistor is connected to the input terminal 21I22 of the auxiliary power supply device 20 through a transmission line. In other words, this photo transistor is supplied with a DC voltage from the power supply device 10 or the sub-power supply circuit unit 22 and outputs a signal using an open collector system in accordance with emission/no-emission of the light emitting diode. For this reason, the resistance element R1 included in the power supply system 1 is a resistance element that is used for limiting supply of electric power that is excessive for the photo transistor. In addition, an output destination of this signal may be another circuit included in the auxiliary power supply device 20, an external circuit, an external device, or the like. In FIG. 1, the output destination of this signal is omitted.

Next, the configuration of the sub-power supply circuit unit 22 will be described.

The sub-power supply circuit unit 22 may have any configuration as long as it is a configuration in which an input side is connected to the power supply device 10, an output side is connected to the load LD, and an output voltage is able to be supplied to another circuit unit in accordance with electric power supplied from the power supply device 10. Hereinafter, a case in which the sub-power supply circuit unit 22 includes a DC/DC converter 221 of an insulation type having a transformer will be described as one example. In addition, the sub-power supply circuit unit 22 may be configured to include other circuit elements, other circuits, other devices, other members, and the like in addition to the DC/DC converter 221.

A power supply terminal on a high electric potential side among two power supply terminals included in the DC/DC converter 221 is connected to the power supply terminal 22I11 of the sub-power supply circuit unit 22 through a transmission line. In addition, other circuit elements, other circuits, other devices, other members, and the like may be configured to be provided between these two power supply terminals unless the function of the power supply system 1 is impaired.

A power supply terminal on a low electric potential side among two power supply terminals included in the DC/DC converter 221 is connected to the power supply terminal 22I12 of the sub-power supply circuit unit 22 through a transmission line. In addition, other circuit elements, other circuits, other devices, other members, and the like may be configured to be provided between these two power supply terminals unless the function of the power supply system 1 is impaired.

An output terminal on a high electric potential side among two output terminals included in the DC/DC converter 221 is connected to the output terminal 22O11 of the sub-power supply circuit unit 22 through a transmission line. In addition, other circuit elements, other circuits, other devices, other members, and the like may be configured to be provided between these two output terminals unless the function of the power supply system 1 is impaired.

An output terminal on a low electric potential side among the two output terminals included in the DC/DC converter 221 is connected to the output terminal 22O12 of the sub-power supply circuit unit 22 through a transmission line. In addition, other circuit elements, other circuits, other devices, other members, and the like may be configured to be provided between these two output terminals unless the function of the power supply system 1 is impaired.

In other words, the DC/DC converter 221 is supplied with a DC voltage after conversion performed by the AC/DC converter 111 of the power supply device 10 from the power supply device 10. Then, the DC/DC converter 221 converts the supplied DC voltage into a DC voltage of a magnitude determined in advance and outputs the DC voltage after the conversion to another circuit unit as an output voltage. In the example illustrated in FIG. 1, the DC/DC converter 221 outputs the output voltage to the information circuit unit 215 of the auxiliary power supply circuit unit 21 and the switchover circuit unit 13 of the power supply device 10. In other words, each of the information circuit unit 215 and the switchover circuit unit 13 is an example of the other circuit unit.

In addition, a switching element may be configured to be connected between the switchover circuit unit 13 and the DC/DC converter 221. In such a case, a user of the power supply system 1 can perform an operation of whether or not the control circuit unit 12 of the power supply device 10 is to be enabled through a switching element. In accordance with this, the power supply system 1 can improve a user's convenience.

In accordance with the configuration described above, in the power supply system 1, the auxiliary power supply circuit unit 21 and the sub-power supply circuit unit 22 are integrally configured. For this reason, in the power supply system 1, the installation area can be smaller than that of a case in which the auxiliary power supply circuit unit 21 and the sub-power supply circuit unit 22 are connected to the power supply device 10 as different devices. In other words, the power supply system 1 can inhibit an increase in the size of the entire power supply system 1. This means that the auxiliary power supply device 20 can inhibit an increase in the size of the entire power supply system 1 including both the auxiliary power supply circuit unit 21 and the sub-power supply circuit unit 22 more than in a case in which the auxiliary power supply circuit unit 21 and the sub-power supply circuit unit 22 are separate bodies. In addition, this also means that an increase in the size of the power supply device 10 can be inhibited in a case in which the auxiliary power supply device 20 and the power supply device 10 are integrally configured. The inhibition of an increase in the size of each of the power supply device 10 and the power supply system 1 also leads to the versatility of each of the auxiliary power supply device 20, the power supply device 10, and the power supply system 1.

In addition, as in this embodiment, in a case in which the auxiliary power supply circuit unit 21 and the sub-power supply circuit unit 22 are integrally configured, members in the vicinity of power supply terminals of the auxiliary power supply circuit unit 21 and the sub-power supply circuit unit 22 can be configured to be common. Particularly, as illustrated in FIG. 1, in a case in which the auxiliary power supply circuit unit 21 and the sub-power supply circuit unit 22 are connected in parallel with the power supply device 10, by configuring the members in the vicinity of the power supply terminals to be common, the number of components can be reduced. This also leads to inhibition of an increase in the manufacturing cost, which is desirable.

In addition, as in this embodiment, in a case in which the auxiliary power supply circuit unit 21 and the sub-power supply circuit unit 22 are integrally configured, even in a case in which supply of electric power to the power supply device 10 is shut off, until the charged voltage of the first capacitor of the charging/discharging circuit unit 211 becomes lower than a predetermined voltage, the sub-power supply circuit unit 22 can be driven using a DC voltage supplied from the charging/discharging circuit unit 211 of the auxiliary power supply circuit unit 21. As in a conventional case, in a case in which the auxiliary power supply circuit unit 21 and the sub-power supply circuit unit 22 are connected to the power supply device 10 as different devices, the sub-power supply circuit unit 22 cannot be driven in accordance with shut-off of supply of electric power to the power supply device 10. This is not desirable for protection of other circuits and other devices driven in accordance with supply of electric power from the sub-power supply circuit unit 22. In other words, as in this embodiment, it can be regarded to be preferable to integrally configure the auxiliary power supply circuit unit 21 and the sub-power supply circuit unit 22 for protection of other circuits and other devices driven in accordance with supply of electric power from the sub-power supply circuit unit 22.

Figure 2:
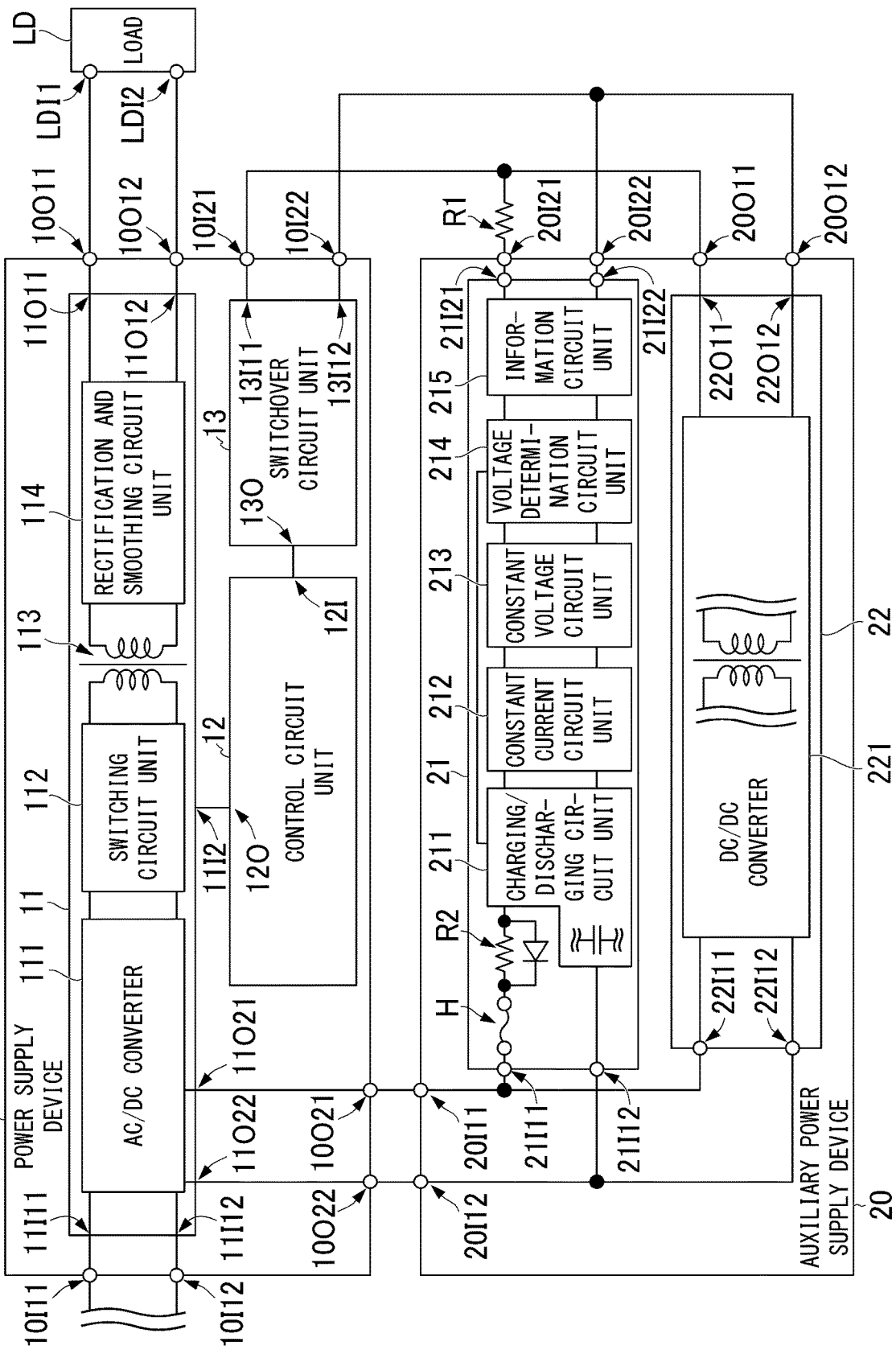
FIG. 2 is a diagram illustrating another example of the configuration of the power supply system 1.

In addition, the connection pattern of the power supply system 1 illustrated in FIG. 1 may be the connection pattern illustrated in FIG. 2. FIG. 2 is a diagram illustrating another example of the configuration of the power supply system 1.

In the example illustrated in FIG. 2, the switchover circuit unit 13 is not supplied with a DC voltage from the power supply circuit unit 11, and each of the information circuit unit 215 and the switchover circuit unit 13 is supplied with a DC voltage from the sub-power supply circuit unit 22. In other words, in this example, the output terminal 10O11 of the power supply device 10 is connected to the power supply terminal LDI1 of the load LD by a transmission line. In this example, the output terminal 10O11 is not connected to each of the input terminal 10I21 of the power supply device 10, the resistance element R1, and the output terminal 20O11 of the auxiliary power supply device 20. In this example, the output terminal 10O12 of the power supply device 10 is connected to the power supply terminal LDI2 of the load LD by a transmission line. In this example, the output terminal 10O12 is not connected to each of the input terminal 10I22 of the power supply device 10 and the input terminal 20I22 and the output terminal 20O12 of the auxiliary power supply device 20. In accordance with these, in this example, the power supply system 1 does not include the diode D1 and the diode D2.

Here, as in the examples illustrated in FIGS. 1 and 2, in a case in which the power supply circuit unit 11 of the power supply device 10 is an insulation type (in other words, the power supply device 10 has a transformer), the sub-power supply circuit unit 22 is supplied with electric power from the primary side of the power supply circuit unit 11. For this reason, in this case, the sub-power supply circuit unit 22 is connected to each of the primary side and the secondary side of the power supply circuit unit 11, and thus, as in this example, it is preferable that the sub-power supply circuit unit 22 is an insulation type (in other words, has a transformer). In addition, in a case in which the power supply circuit unit 11 is a non-insulation type, the sub-power supply circuit unit 22 may be either a non-insulation type or an insulation type.

Another Example of Power Supply Device that is a Target to which Auxiliary Power Supply Device is Connected Hereinafter, another example of a power supply device that is a target to which the auxiliary power supply device 20 described above is connected will be described.

Figure 3:
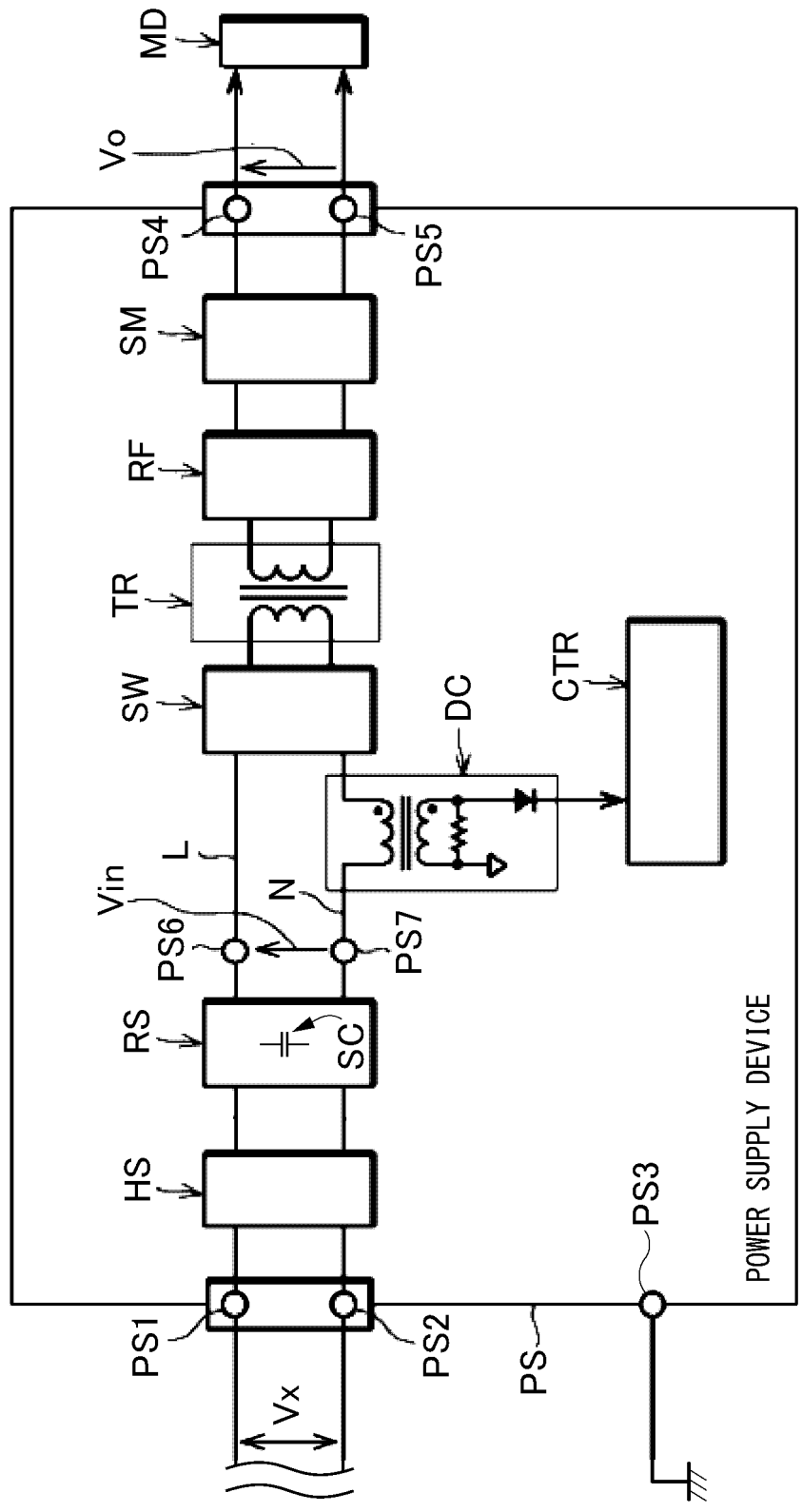
FIG. 3 is a diagram illustrating an example of the configuration of a power supply device PS that is a target to which an auxiliary power supply device 20 is connected.

FIG. 3 is a diagram illustrating an example of the configuration of a power supply device PS that is a target to which the auxiliary power supply device 20 is connected. The power supply device PS illustrated in FIG. 3 is a power supply device to which a medical device MD is connected as a load. The medical device MD is a medical device operating based on a DC voltage Vo output by the power supply device PS and, for example, is a therapeutic device, a diagnosis device, an analysis device, or the like but is not limited thereto. In addition, for example, the therapeutic device is a low frequency treatment device, an electrotherapeutic device, or the like. For example, the diagnosis device is a CT (Computed Tomography), a MRI (Magnetic Resonance Imaging), or the like. For example, the analysis device is an electrometric titration device, an X-ray diffractometer, or the like.

The power supply device PS has seven terminals including a power supply terminal PS1, a power supply terminal PS2, a frame ground terminal PS3, an output terminal PS4, an output terminal PS5, a connection terminal PS6, and a connection terminal PS7. For example, a commercial power supply (for example, the power supply P described above) is connected to the power supply terminal PS1 and the power supply terminal PS2, and the power supply terminal PS1 and the power supply terminal PS2 are supplied with an AC voltage Vx from the commercial power supply. For example, the frame ground terminal PS3 is grounded. In addition, for example, power supply terminals of the medical device MD described above are connected to the output terminal PS4 and the output terminal PS5. In other words, the power supply device PS supplies a DC voltage Vo from the output terminal PS4 and the output terminal PS5 to the power supply terminals of the medical device MD. In addition, for example, the auxiliary power supply device 20 is connected to the connection terminal PS6 and the connection terminal PS7. More specifically, the power supply terminal 20I11 of the auxiliary power supply device 20 is connected to the connection terminal PS6. On the other hand, the power supply terminal 20I12 of the auxiliary power supply device 20 is connected to the connection terminal PS7.

Here, the power supply device PS illustrated in FIG. 3, for example, includes a fuse unit HS, a rectification and smoothing circuit unit RS, a switching circuit unit SW, a transformer TR, a rectification circuit unit RF, and a smoothing circuit unit SM. In addition, the power supply device PS includes an input transmission line L connected to the power supply terminal PS1 and an input transmission line N connected to the power supply terminal PS2.

In order for the power supply device PS to satisfy a medical standard to be satisfied as a power supply device connected to the medical device MD, the fuse unit HS is provided in the power supply device PS. The fuse unit HS has a fuse disposed on the input transmission line L connecting the power supply terminal PS1 and the rectification and smoothing circuit unit RS and a fuse disposed on the input transmission line N connecting the power supply terminal PS2 and the rectification and smoothing circuit unit RS. In addition, the power supply device PS may be configured to include a breaker in place of one or both of these two fuses.

The rectification and smoothing circuit unit RS generates a pulsating voltage acquired by rectifying an AC voltage Vx supplied from two transmission lines including the input transmission line L connected to the power supply terminal PS1 through the fuse unit HS and the input transmission line N connected to the power supply terminal PS2 through the fuse unit HS, smooths the generated pulsating voltage, and outputs a DC voltage Vin. For this reason, the rectification and smoothing circuit unit RS includes a smoothing capacitor SC that supplies a voltage for smoothing a pulsating voltage after rectification. Here, one of two terminals included in the smoothing capacitor SC is connected to the input transmission line L. In addition, the other of the two terminals included in the smoothing capacitor SC is connected to the input transmission line N. In FIG. 3, in order to prevent complications of the drawing, illustration of a transmission line connecting the smoothing capacitor SC and each of the input transmission line L and the input transmission line N is omitted. In this way, the rectification and smoothing circuit unit RS is connected to the fuse unit HS disposed in a previous stage of the rectification and smoothing circuit unit RS through the input transmission line L and the input transmission line N. In addition, the rectification and smoothing circuit unit RS is connected to a connection terminal PS6 disposed in a next stage of the rectification and smoothing circuit unit RS through the input transmission line L. The rectification and smoothing circuit unit RS is connected to a connection terminal PS7 disposed in a next stage of the rectification and smoothing circuit unit RS through the input transmission line L. For this reason, the rectification and smoothing circuit unit RS applies the DC voltage Vin after smoothing between the connection terminal PS6 and the connection terminal PS7. In addition, the rectification and smoothing circuit unit RS may be configured to further include a power factor improvement circuit (a power factor correction (PFC) circuit).

In addition, the connection terminal PS6 is connected to one of two input terminals included in the switching circuit unit SW through the input transmission line L. The connection terminal PS7 is connected to the other of the two input terminals included in the switching circuit unit SW through the input transmission line L. For this reason, the DC voltage Vin output from the rectification and smoothing circuit unit RS is supplied to the switching circuit unit SW. The switching circuit unit SW, for example, includes a plurality of switching elements connected in a bridge pattern and outputs an AC voltage generated by operations of a plurality of these switching elements controlled by a control unit CTR based on a DC voltage supplied from the rectification and smoothing circuit unit RS to a primary winding of the transformer TR. For this reason, the switching circuit unit SW is connected to one of two terminals included in the winding through the input transmission line L and is connected to the other of the two terminals included in the winding through the input transmission line N.

The transformer TR is reinforced insulated transformer. The reason the transformer TR is reinforced insulated is for enabling the power supply device PS to satisfy the medical standard described above. A secondary winding of the transformer TR is connected to the rectification circuit unit RF through a transmission line and supplies an AC voltage to the rectification circuit unit RF.

The rectification circuit unit RF generates a pulsating voltage by rectifying an AC voltage supplied from the transformer TR and supplies the generated pulsating voltage to the smoothing circuit unit SM through a transmission line.

The smoothing circuit unit SM generates a DC voltage by smoothing the pulsating voltage supplied from the rectification circuit unit RF and applies the generated DC voltage Vo between the output terminal PS4 and the output terminal PS5.

A current detection circuit unit DC detects a current flowing through the input transmission line N connecting the connection terminal PS7 and the switching circuit unit SW. Then, the current detection circuit unit DC outputs a signal corresponding to the magnitude of the detected current to the control unit CTR.

For example, the control unit CTR is a microcomputer. The control unit CTR controls a duty at a drive frequency of the switching circuit unit SW (for example, a pulse width modulation (PWM) control) in accordance with a signal acquired from the current detection circuit unit DC and performs switching of switching elements. In FIG. 3, in order to prevent complications of the drawing, illustration of a transmission line connecting the control unit CTR and the switching circuit unit SW is omitted.

In this way, in the power supply device PS to which the medical device MD is connected as a load, a fuse (or a breaker) included in the fuse unit HS is disposed in each of the input transmission line L and the input transmission line N. For example, the auxiliary power supply device 20 according to the embodiment is connected to such a power supply device PS. In this case, each of the auxiliary power supply device 20, the power supply device PS, and the medical device MD configures one medical system. In this medical system, the power supply device PS includes the fuse unit HS, and the transformer TR is reinforced insulated, whereby the medical system can realize a configuration that is able to acquire the medical standard. In addition, since the auxiliary power supply device 20 is included, this medical system can maintain an output from the power supply device PS for a predetermined time in a case in which supply of electric power to the power supply device PS is shut off. Furthermore, an increase in the size of the auxiliary power supply device 20 is inhibited, and thus an increase in the size of the entire medical system can be inhibited as well.

Many medical devices MD have a function for charging a secondary battery for backup using a DC voltage Vo. For this reason, the power supply device PS may be configured to be able to detect an occurrence of a reverse current from the medical device MD and stop the operation in a case in which an occurrence of the reverse current from the medical device MD has been detected.

Figure 4:
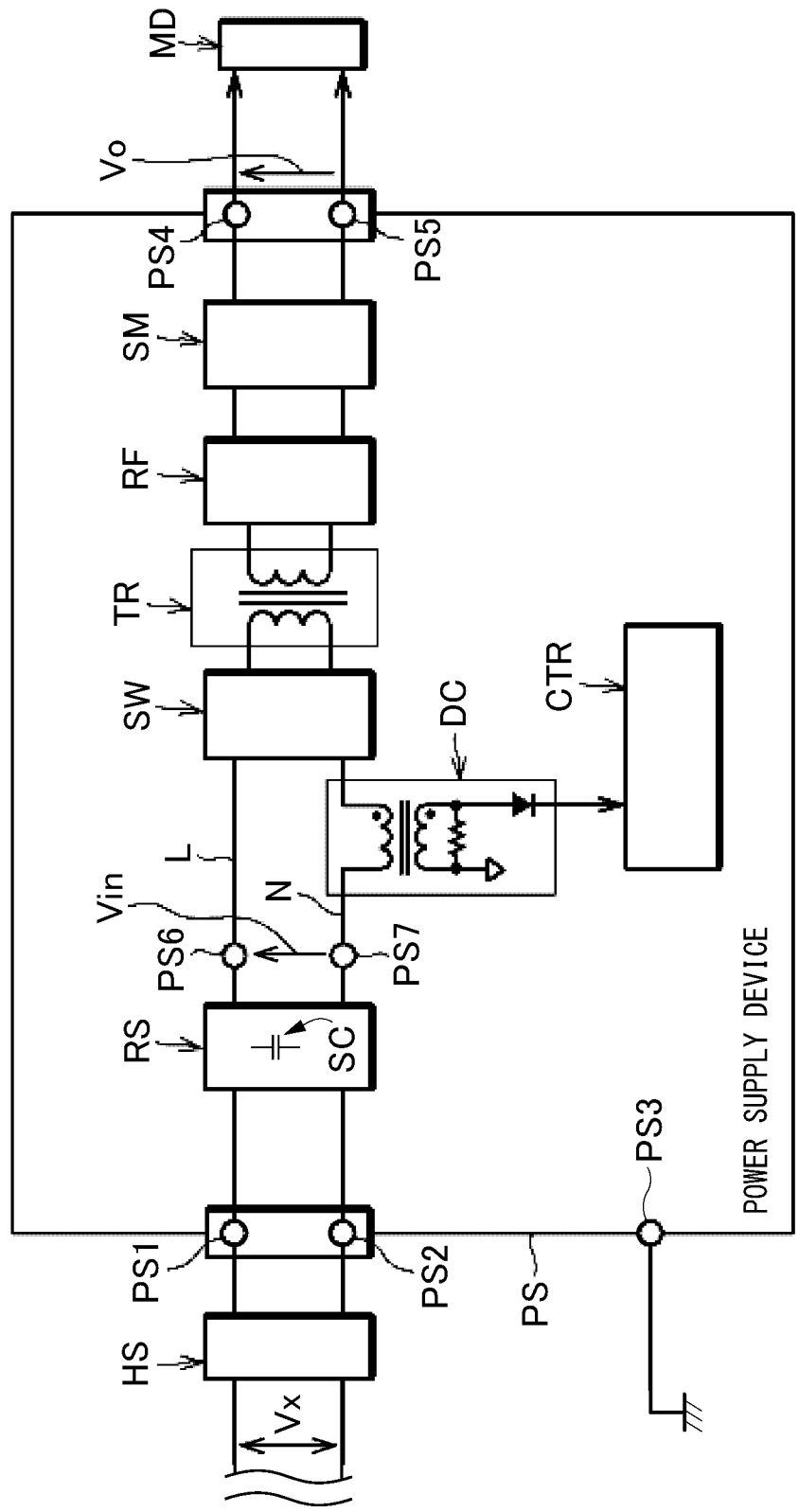
FIG. 4 is a diagram illustrating another example of the configuration of the power supply device PS that is a target to which the auxiliary power supply device 20 is connected.

Here, the power supply device PS illustrated in FIG. 3 internally includes the fuse unit HS. However, as illustrated in FIG. 4, the power supply device PS may be configured to have the fuse unit HS outside. In other words, the fuse unit HS may be configured to be a body that is separate from the power supply device PS and be connected between the power supply device PS and a commercial power supply not illustrated in the drawing. In such a case, the medical system includes the auxiliary power supply device 20, the power supply device PS, the medical device MD, and the fuse unit HS. FIG. 4 is a diagram illustrating another example of the configuration of the power supply device PS that is a target to which the auxiliary power supply device 20 is connected.

As illustrated in FIG. 4, in a case in which the fuse unit HS is provided outside the power supply device PS, one of two fuses included in the fuse unit HS is disposed on a transmission line connecting a commercial power supply not illustrated in the drawing and the power supply terminal PS1. In addition, in a case in which the fuse unit HS is provided outside the power supply device PS, the other of the two fuses included in the fuse unit HS is disposed on a transmission line connecting the commercial power supply not illustrated in the drawing and the power supply terminal PS2.

Figure 5:
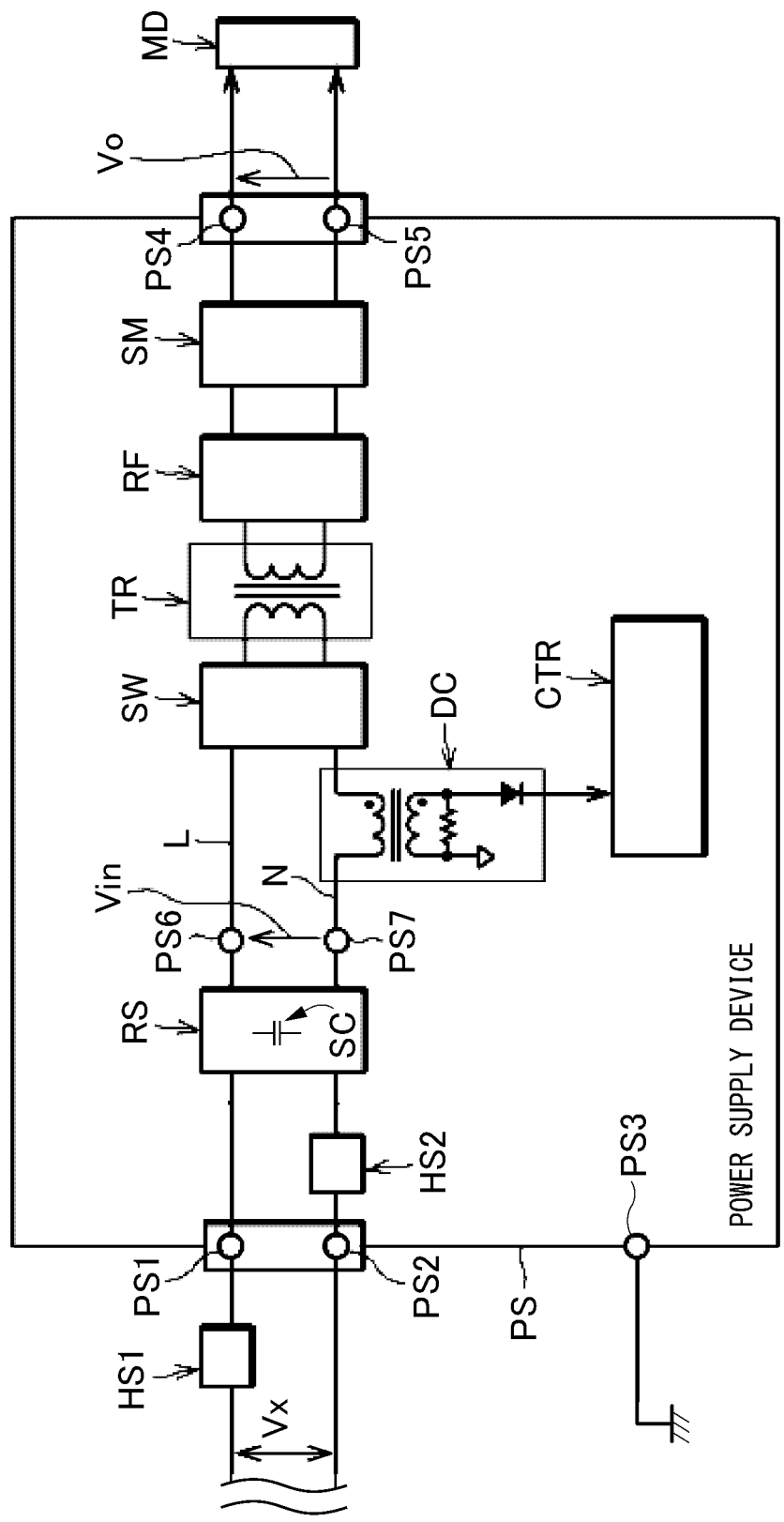
FIG. 5 is diagram illustrating yet another example of the configuration of the power supply device PS that is a target to which the auxiliary power supply device 20 is connected.

In addition, as illustrated in FIG. 6, the power supply device PS may be configured such that one of the two fuses included in the fuse unit HS is disposed inside, and the other of the two fuses included in the fuse unit HS is disposed outside. FIG. 5 is diagram illustrating yet another example of the configuration of the power supply device PS that is a target to which the auxiliary power supply device 20 is connected.

As illustrated in FIG. 5, the power supply device PS may be configured such that a first fuse unit HS1 is disposed on a transmission line connecting a commercial power supply not illustrated in the drawing and a power supply terminal PS1, and a second fuse unit HS2 is disposed on an input transmission line N connecting a power supply terminal PS2 and a rectification and smoothing circuit unit RS.

Here, the first fuse unit HS1 includes a fuse that is disposed on a transmission line connecting the commercial power supply not illustrated in the drawing and the power supply terminal PS1. In addition, the second fuse unit HS2 includes a fuse that is disposed on the input transmission line N connecting the power supply terminal PS2 and the rectification and smoothing circuit unit RS.

As described above, the auxiliary power supply device according to the embodiment (the auxiliary power supply device 20 in the example described above) is an auxiliary power supply device that is connected to a power supply device (the power supply device 10 in the example described above), the auxiliary power supply device including: an auxiliary power supply circuit unit (the auxiliary power supply circuit unit 21 in the example described above) configured to supply electric power to the power supply device in a case in which supply of electric power to the power supply device is shut off; and a sub-power supply circuit unit (the sub-power supply circuit unit 22 in the example described above) having an input side connected to the power supply device and an output side connected to a load (the load LD in the example described above) and configured to supply an output voltage to other circuit units (the information circuit unit 215 and the switchover circuit unit 13 in the example described above) in accordance with electric power supplied from the power supply device. In accordance with this, the auxiliary power supply device can inhibit an increase in the size of an entire system including both an auxiliary power supply circuit unit and a sub-power supply circuit unit.

In addition, in the auxiliary power supply device, a configuration in which an AC voltage is supplied to the power supply device from an external power supply (the power supply P in the example described above), the power supply device includes a converter (the AC/DC converter 111 in the example described above) that converts a voltage supplied from the power supply into a DC voltage, the sub-power supply circuit unit includes an insulating-type DC/DC converter (the DC/DC converter 221 in the example described above) that has a transformer, the DC voltage after conversion performed by the converter is supplied from the power supply device to the DC/DC converter, and the DC/DC converter converts the supplied DC voltage into a DC voltage of a magnitude determined in advance and outputs the DC voltage after the conversion to the other circuit units as the output voltage may be used.

Furthermore, in the auxiliary power supply device, a configuration in which the power supply device further includes: a switching circuit unit (the switching circuit unit 112 in the example described above) configured to convert a DC voltage after conversion performed by the converter into an AC voltage; a first transformer (the transformer 113 in the example described above) configured to transmit the AC voltage after conversion performed by the switching circuit unit from a primary winding to a secondary winding; a rectification and smoothing circuit unit (the rectification and smoothing circuit unit 114 in the example described above) configured to convert an AC voltage supplied from the secondary winding of the first transformer into a DC voltage and output the DC voltage after conversion; a control circuit unit (the control circuit unit 12 in the example described above) configured to control the switching circuit unit; and a switching circuit unit (the switchover circuit unit 13 in the example described above) configured to cause the control circuit unit to perform switching between enabling and disabling of the switching circuit unit in accordance with a supplied voltage, and the sub-power supply circuit unit has an output side connected to the switching circuit unit and supplies the output voltage to the switching circuit unit with the switching circuit unit set as one of the other circuit units may be used.

In addition, in the auxiliary power supply device, a configuration in which the sub-power supply circuit unit is connected in parallel with the auxiliary power supply circuit unit with respect to the power supply device may be used.

Furthermore, in the auxiliary power supply device, a configuration in which the power supply device includes a smoothing capacitor of a primary side (the first smoothing capacitor of the AC/DC converter 111 in the example described above), the auxiliary power supply device includes: a first power supply terminal (the power supply terminal 20I11 in the example described above) that is connected to a first smoothing capacitor terminal among two terminals of the smoothing capacitor; and a second power supply terminal (the power supply terminal 20I12 in the example described above) that is connected to a second smoothing capacitor terminal among the two terminals of the smoothing capacitor, the auxiliary power supply circuit unit and the sub-power supply circuit unit are connected in parallel between the first power supply terminal and the second power supply terminal, and the auxiliary power supply circuit unit includes a first capacitor (the first capacitor of the charging/discharging circuit unit 211 in the example described above) that is charged in accordance with supply of electric power to the power supply device and discharges a discharge current in accordance with discharge of the smoothing capacitor may be used.

In addition, in the auxiliary power supply device, a configuration in which the auxiliary power supply circuit unit further includes: a resistance element (the resistance element R2 in the example described above) that is connected between one of the first power supply terminal and the second power supply terminal and the first capacitor; and a diode (the diode D3 in the example described above) that is connected in parallel with the resistance element between the power supply terminal and the first capacitor, and a direction in which the diode causes a current to flow is a direction from a high electric potential side of the first capacitor to the power supply terminal may be used.

In addition, in the auxiliary power supply device, a configuration in which, in a case in which the first smoothing capacitor terminal and the first power supply terminal are connected to each other, and the second smoothing capacitor terminal and the second power supply terminal are connected to each other, the first capacitor discharges a discharge current in accordance with discharge of the smoothing capacitor may be used.

Furthermore, in the auxiliary power supply device, a configuration in which the auxiliary power supply circuit unit includes: a charging/discharging circuit unit (the charging/discharging circuit unit 211 in the example described above) including the first capacitor; a constant current circuit unit (the constant current circuit unit 212 in the example described above) configured to output a current of a magnitude determined in advance based on a voltage applied from the smoothing capacitor or the first capacitor; a constant voltage circuit unit (the constant voltage circuit unit 213 in the example described above) configured to output a voltage of a magnitude determined in advance based on a current output from the constant current circuit unit; a voltage determination circuit unit (the voltage determination circuit unit 214 in the example described above) configured to determine whether or not a detected voltage of the first capacitor or a detected voltage of the smoothing capacitor is lower than a reference voltage generated based on a voltage output from the constant voltage circuit unit; and a information circuit unit (the information circuit unit 215 in the example described above) configured to inform of information indicating a determination result acquired by the voltage determination circuit unit, and the information circuit unit is included in the other circuit units may be used.

As above, although the embodiment of the present invention has been described in detail with reference to the drawings, a specific configuration is not limited to this embodiment, and modifications, substitutions, omissions, and the like can be made without departing from the spirit or scope of the present invention.

EXPLANATION OF REFERENCES

1 Power supply system
10 Power supply device
11 Power supply circuit unit
12 Control circuit unit
13 Switchover circuit unit
20 Auxiliary power supply device
21 Auxiliary power supply circuit unit
22 Sub-power supply circuit unit
111 AC/DC converter
112 Switching circuit unit
113 Transformer
114 Rectification and smoothing circuit unit
211 Charging/discharging circuit unit
212 Constant current circuit unit
213 Constant voltage circuit unit
214 Voltage determination circuit unit
215 Information circuit unit
221 DC/DC converter
CTR Control unit
D1, D2, D3 Diode
DC Current detection circuit unit
H Fuse
HS Fuse unit
HS1 First fuse unit
HS2 Second fuse unit
LD Load
MD Medical device
P Power supply
PS Power supply device
R1, R2 Resistance element
RF Rectification circuit unit
RS Rectification and smoothing circuit unit
SC Smoothing capacitor
SM Smoothing circuit unit
SW Switching circuit unit
TR Transformer

What is claimed is:
1. A power supply system comprising:
a power supply device; and
an auxiliary power supply device,
wherein an AC voltage is supplied to the power supply device from an external power supply;
the power supply device comprises a converter, a switching circuit unit, a first transformer, a rectification and smoothing circuit unit, a control circuit unit, and a switchover circuit unit,
the converter converts a voltage supplied from the external power supply into a DC voltage,
the switching circuit unit converts the DC voltage after the conversion performed by the converter into an AC voltage,
the first transformer transmits the AC voltage after conversion performed by the switching circuit unit from a primary winding to a secondary winding,
the rectification and smoothing circuit unit converts an AC voltage supplied from the secondary winding of the first transformer into a DC voltage and output the DC voltage after conversion,
the control circuit unit controls the switching circuit unit,
the switchover circuit unit causes the control circuit unit to perform switching between enabling and disabling of the switching circuit unit in accordance with a supplied voltage,
the auxiliary power supply device is connected to the power supply device,
the auxiliary power supply device comprises the auxiliary power supply circuit unit, and a sub-power supply circuit unit,
the auxiliary power supply circuit unit supplies electric power to the power supply device in a case in which supply of electric power to the power supply device is shut off,
the sub-power supply circuit unit has an input side connected to the power supply device and an output side connected to a load and supplies an output voltage to other circuit units in accordance with electric power supplied from the power supply device, and includes an insulating-type DC/DC converter that has a transformer,
the DC voltage after conversion performed by the converter is supplied from the power supply device to the DC/DC converter,
the DC/DC converter converts the supplied DC voltage into a DC voltage of a magnitude determined in advance and outputs the DC voltage after the conversion to the other circuit units as the output voltage, and
the sub-power supply circuit unit has an output side connected to the switchover circuit unit and supplies the output voltage to the switchover circuit unit with the switchover circuit unit as one of the other circuit units.
2. The power supply system according to claim 1, wherein the sub-power supply circuit unit is connected in parallel with the auxiliary power supply circuit unit with respect to the power supply device.
3. The power supply system according to claim 2,
wherein the power supply device includes a smoothing capacitor of a primary side,
the auxiliary power supply device comprises:
a first power supply terminal that is connected to a first smoothing capacitor terminal among two terminals of the smoothing capacitor; and
a second power supply terminal that is connected to a second smoothing capacitor terminal among the two terminals of the smoothing capacitor, the auxiliary power supply circuit unit and the sub-power supply circuit unit are connected in parallel between the first power supply terminal and the second power supply terminal, and the auxiliary power supply circuit unit includes a first capacitor that is charged in accordance with supply of electric power to the power supply device and discharges a discharge current in accordance with discharge of the smoothing capacitor.

4. The power supply system according to claim 3, wherein the auxiliary power supply circuit unit further comprises:
 a resistance element that is connected between one of the first power supply terminal and the second power supply terminal and the first capacitor; and
 a diode that is connected in parallel with the resistance element between the power supply terminal and the first capacitor, and
 a direction in which the diode causes a current to flow is a direction from a high electric potential side of the first capacitor to the power supply terminal.

5. The power supply system according to claim 3, wherein, in a case in which the first smoothing capacitor terminal and the first power supply terminal are connected to each other, and the second smoothing capacitor terminal and the second power supply terminal are connected to each other, the first capacitor discharges a discharge current in accordance with discharge of the smoothing capacitor.

6. The power supply system according to claim 4, wherein, in a case in which the first smoothing capacitor terminal and the first power supply terminal are connected to each other, and the second smoothing capacitor terminal and the second power supply terminal are connected to each other, the first capacitor discharges a discharge current in accordance with discharge of the smoothing capacitor.

7. The power supply system according to claim 3, wherein the auxiliary power supply circuit unit comprises:
 a charging/discharging circuit unit including the first capacitor;
 a constant current circuit unit configured to output a current of a magnitude determined in advance based on a voltage applied from the smoothing capacitor or the first capacitor;
 a constant voltage circuit unit configured to output a voltage of a magnitude determined in advance based on a current output from the constant current circuit unit;
 a voltage determination circuit unit configured to determine whether or not a detected voltage of the first capacitor or a detected voltage of the smoothing capacitor is lower than a reference voltage generated based on a voltage output from the constant voltage circuit unit; and
 a information circuit unit configured to inform of information indicating a determination result acquired by the voltage determination circuit unit, and
the information circuit unit is included in the other circuit units.

8. The power supply system according to claim 4, wherein the auxiliary power supply circuit unit comprises:
 a charging/discharging circuit unit including the first capacitor;
 a constant current circuit unit configured to output a current of a magnitude determined in advance based on a voltage applied from the smoothing capacitor or the first capacitor;
 a constant voltage circuit unit configured to output a voltage of a magnitude determined in advance based on a current output from the constant current circuit unit;
 a voltage determination circuit unit configured to determine whether or not a detected voltage of the first capacitor or a detected voltage of the smoothing capacitor is lower than a reference voltage generated based on a voltage output from the constant voltage circuit unit; and
 a information circuit unit configured to inform of information indicating a determination result acquired by the voltage determination circuit unit, and
the information circuit unit is included in the other circuit units.

9. The power supply system according to claim 5, wherein the auxiliary power supply circuit unit comprises:
 a charging/discharging circuit unit including the first capacitor;
 a constant current circuit unit configured to output a current of a magnitude determined in advance based on a voltage applied from the smoothing capacitor or the first capacitor;
 a constant voltage circuit unit configured to output a voltage of a magnitude determined in advance based on a current output from the constant current circuit unit;
 a voltage determination circuit unit configured to determine whether or not a detected voltage of the first capacitor or a detected voltage of the smoothing capacitor is lower than a reference voltage generated based on a voltage output from the constant voltage circuit unit; and
 a information circuit unit configured to inform of information indicating a determination result acquired by the voltage determination circuit unit, and
the information circuit unit is included in the other circuit units.

10. A medical system comprising:
the power supply system according to claim 1; and
a medical device connected to the power supply device as the load.

11. The medical system according to claim 10, wherein the power supply device includes a fuse or a breaker disposed in at least one of two input transmission lines of a primary side of the power supply device.

* * * * *